United States Patent [19]

Rheinecker

[11] 4,087,271

[45] May 2, 1978

[54] 1,2-BIS (THIOALKYL) ALKANES AND DERIVATIVES THEREOF AS ABSCISSION AGENTS

[75] Inventor: Tom Conrad Rheinecker, Green Township, Hamilton County, Ohio

[73] Assignee: The Procter & Gamble Company, Cincinnati, Ohio

[21] Appl. No.: 710,353

[22] Filed: Jul. 30, 1976

Related U.S. Application Data

[63] Continuation-in-part of Ser. No. 676,762, Apr. 14, 1976, abandoned.

[51] Int. Cl.[2] .............................................. A01N 9/14

[52] U.S. Cl. .......................................... 71/98; 71/103; 71/72

[58] Field of Search .................................... 71/98, 103

[56] References Cited

U.S. PATENT DOCUMENTS

| | | | |
|---|---|---|---|
| 2,658,038 | 11/1953 | Proell | 252/161 |
| 3,124,447 | 3/1964 | Wineman et al. | 71/98 |
| 3,901,683 | 8/1975 | Limpel et al. | 71/98 |
| 3,941,826 | 3/1976 | Martin | 260/465 R |

OTHER PUBLICATIONS

Parr et al., Botan. Gaz., vol. 126(2), 1965, pp. 86 and 92.
Stembridge et al., Chem. Abst., vol. 72, (1970), 120305m.

*Primary Examiner*—Lewis Gotts
*Assistant Examiner*—Catherine L. Mills
*Attorney, Agent, or Firm*—Ronald L. Hemingway; Richard C. Witte

[57] ABSTRACT

Fruit abscission is induced by application to a fruit bearing plant of particular 1,2-bis(thioalkyl)alkanes and derivatives thereof optionally in combination with nonphytotoxic surfactant different from said alkanes and derivatives. The alkanes and derivatives have the structural formula $$\underset{\displaystyle X}{\underset{|}{RCH}}-CH_2-X$$

wherein R is an alkyl group having 8–10 carbon atoms and both X's are the same and are selected from the group consisting of thiomethyl, thioethyl, sulfinylmethyl, sulfinylethyl, sulfonylmethyl, and sulfonylethyl.

9 Claims, No Drawings

1,2-BIS (THIOALKYL) ALKANES AND DERIVATIVES THEREOF AS ABSCISSION AGENTS

CROSS-REFERENCE TO RELATED APPLICATION

This application is a continuation-in-part application of U.S. application Ser. No. 676,762, filed Apr. 14, 1976, entitled "1,2-bis (THIOMETHYL) ALKANES AND DERIVATIVES THEREOF AS ABSCISSION AGENTS, now abandoned."

BACKGROUND OF THE INVENTION

This invention relates to application to fruit bearing plants of particular agents to induce fruit abscission. The invention is particularly useful where the fruits are citrus fruits, especially oranges.

The ability of plants to slough off organs, such as fruit, by an active separation of cells is described by plant physiologists as the process of abscission. Abscission, unaided by mechanical or chemical agents, results from the formation of a starch-filled layer of cells in the area of the fruit rind separating the stem from the fruit. This starch-filled layer is known as the abscission layer. Abscission occurs as the cells in the abscission layer begin to separate, eventually dropping the fruit from the stem. Abscission generally occurs shortly after the fruit has fully matured.

Commercial harvesting of fruit bearing plants very often requires deviation from the natural abscission cycle. Many varieties of fruit bearing plants, such as citrus, reach maturity and are harvested without completion of the abscission cycle. Moreover, citrus fruit can actually regreen, i.e., become more tightly attached to the fruit stem, as acceptable maturity standards for eating quality are reached.

When fruit is mechanically harvested without chemical aids and the cells of the abscission layer have not begun to separate or the fruit has begun to regreen, a great deal of force is required to remove the fruit. Often when adequate force to remove the fruit is applied to the fruit or fruit bearing plant, a break or tear can take place and a plug of tissue may be removed from the fruit rind; sometimes the fruit stem is broken, leaving a jagged woody stem attached to the fruit; or the fruit bearing plant itself is injured.

Several chemicals have been used to regulate the abscission process of fruit bearing plants in attempts to facilitate harvesting. Such chemicals are called, in general terms, harvesting aids or abscission agents. Typical abscission agents are formulated to loosen fruit at the time of harvest.

Abscission agents disclosed in the patent literature include pyridine-N-oxides (U.S. Pat. No. 3,810,752), alkylamines (U.S. Pat. No. 3,867,127), and hydroxylamines (U.S. Pat. No. 3,869,278).

Abscission agents that are the subject of pending patent applications are bis(2-pyridine-N-oxide)disulfides (Bednarz and Otten, Ser. No. 602,610 filed Aug. 7, 1975) now abandoned; bis(2-pyridine-N-oxide)disulfoxides (Otten and Rheinecker Ser. No. 602,626 filed Aug. 7, 1975; bis(2-pyridine-N-oxide)disulfones (Otten and Rheinecker Ser. No. 602,335 filed Aug. 6, 1975 now abandoned); and alkyl and alkenyl methyl and ethyl sulfides and derivatives thereof (Otten, Rheinecker and Logan, Ser. No. 676,832 filed Apr. 14, 1976 now abandoned).

It is an object of the present invention to provide a method of inducing abscission utilizing agents of different chemical structure from the agents set forth above.

It is an object of this invention in one of its preferred aspects to provide a method of inducing abscission utilizing such agents in combination with non-phytotoxic surfactants.

It is an object of this invention in another of its preferred aspects to provide novel compositions for admixture with water for application to fruit bearing plants to induce fruit abscission.

These and other objects and advantages of the invention will be evident from the following detailed description.

DETAILED DESCRIPTION

The method of inducing fruit abscission of the present invention comprises applying to fruit bearing plants an effective amount of agent having the structural formula RCH—CH₂—X with X on the CH $$\begin{array}{l} RCH-CH_2-X \\ \ \ | \\ \ \ X \end{array}$$

wherein R is an alkyl group having 8–10 carbon atoms and both X's are the same and are selected from the group consisting of thiomethyl (i.e.,—$SCH_3$), thioethyl (i.e.,—$SC_2H_5$), sulfinylmethyl (i.e.,

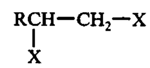

sulfinylethyl (i.e.,

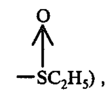

sulfonlymethyl (i.e.,

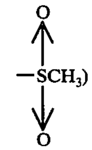

and sulfonylethyl (i.e.,

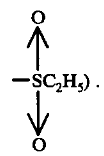

Preferred compounds are those wherein X is thiomethyl, sulfinylmethyl or sulfonylmethyl.

Specific examples of compounds useful within the scope of the invention and having the above structural formula where X is thiomethyl or thioethyl are 1,2-bis(-thiomethyl)decane, 1,2-bis(thiomethyl)undecane, 1,2-bis(thiomethyl)dodecane, 1,2bis(thioethyl)decane, 1,2-bis(thioethyl undecane) and 1,2-bis(thioethyl)dodecane.

Specific examples of compounds useful within the scope of the invention and having the above structural formula where X is sulfinylmethyl or sulfinylethyl are 1,2-bis(sulfinylmethyl)decane, 1,2-bis(sulfinylmethyl-)undecane, 1,2-bis(sulfinylmethyl)dodecane, 1,2-bis(sulfinylethyl)decane, 1,2-bis(sulfinylethyl)undecane and 1,2-bis(sulfinylethyl)dodecane.

Specific examples of compounds useful within the scope of the invention and having the above structural formula where X is sulfonylmethyl are 1,2-bis(sulfonylmethyl)decane, 1,2-bis(sulfonylmethyl)undecane, 1,2-bis(sulfonylmethyl)dodecane, 1,2-bis)sulfonylethyl)decane, 1,2-bis(sulfonylethyl)undecane and 1,2-bis(sulfonylethyl)dodecane.

Highly preferred compounds for use within the scope of the present invention are those having the above structural formula wherein R is an alkyl group containing 10 carbon atoms and the short chain alkyl is methyl. The most preferred compounds are 1,2-bis(thiomethyl)-dodecane and 1,2-bis(sulfinylmethyl)dodecane.

The 1,2bis(thioalkyl)alkane abscission agents described above are readily prepared, for example, by reacting the appropriate 1-alkyne with methyl or ethyl mercaptan (the molar ratio of alkyne to mercaptan being approximately 1 to 2) under pressure (such as 1000 psig) and at a temperature of, for example, 100° C in the presence of 2,2'-azobis(2-methylpropionitrile), i.e., ABN.

The 1,2-bis(sulfinylalkyl)alkane abscission agents described above are readily prepared, for example, by oxidizing the appropriate 1,2-bis(thioalkyl)alkane, (for example a 1,2-bis-(thiomethyl)alkane prepared by the method described in the above paragraph). This reaction can be carried out in dilute ethanol utilizing 30% hydrogen peroxide as an oxidizing agent.

The 1,2-bis(sulfonylalkyl)alkane abscission agents described above are readily prepared by peroxide treatment of the appropriate 1,2-bis(sulfinylalkyl)alkane or by treating an appropriate 1,2-bis(thioalkyl)alkane with a stronger oxidizing agent such as sodium hypochlorite.

As used hereinafter, the term "abscission agent(s)" refers only to the agents having the structural formula

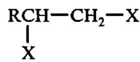

described in more detail above.

As indicated above, an effective amount of abscission agent is applied. This amount ordinarily ranges from about 0.1 pound per acre to 50 pounds per acre.

The abscission agents are preferably formulated into compositions for application. The agents which are normally liquids (for example, the 1,2-bis(thiomethyl)alkanes) or 1,2-bis(thioethyl)alkanes) are advantageously formulated as emulsions for example in water or other polar liquid. The agents which are normally solids (for example, the 1,2-bis(sulfinylmethyl)alkanes, 1,2-bis(sulfinylethyl)alkanes, 1,2-bis(sulfonylmethyl)alkanes) and 1,2-bis(sulfonylethyl)alkanes) are advantageously formulated as suspensions, for example in water or other polar liquid, or as solid compositions (dusts).

The formulations which are applied to fruit bearing plants within the scope of the present invention ordinarily contain from about 10 parts per million to about 10,000 parts per million of abscission agent.

The abscission agents are advantageously formulated for use within the scope of the present invention in admixture with mon-phytotoxic, that is plant compatible surfactant, to provide either solid or liquid (including a suspension of a solid in a liquid phase) formulations. (The abscission agents herein can have surfactant properties; the surfactants referred to herein are different from the abscission agents used herein). The surfactants can have a positive effect on the inducing of abscission. Moreover, the surfactant acts as a dispersing or emulsifying agent if the combination of abscission agent and surfactant is admixed with water or other polar liquid for application to plants. In general, compositions for use within the scope of the method of the present invention or for admixture with water or other polar liquid for such use contain abscission agent and surfactant in a weight ratio of abscission agent to surfactant ranging from about 1:400 to about 10:1.

Surfactants for use as described above can be anionic, cationic, nonionic, ampholytic, and zwitterionic types.

Examples of suitable anionic surfactants for use herein are alkali metal (e.g. sodium), ammonium and amine salts of fatty alcohol sulfates having from 8–18 carbon atoms in the fatty chain and sodium salts of alkyl benzene sulfonates having from 9 to 15 carbon atoms in the alkyl chain.

Examples of suitable nonionic surfactants are the polyoxyethylene adducts of fatty alcohols having 10 to 18 carbon atoms, and the polyethylene oxide condensates of alkyl phenols wherein the alkyl chain contains from about 6 to 12 carbon atoms and the amount of ethylene oxide condensed onto each mole of alkyl phenol is from about 5 to 25 moles, and the polyethylene oxide condensates of sorbitan esters (for example, surfactants sold under the tradename Tween) wherein the amount of ethylene oxide condensed onto each mole of sorbitan ester is about 10 to 40 moles.

Examples of suitable cationic surfactants are dimethyl dialkyl quaternary ammonium salts wherein the alkyl chains contain from about 8 to 18 carbon atoms and the salt forming anion is a halogen.

Examples of suitable ampholytic surfactants are derivatives of aliphatic secondary or tertiary amines in which one of the aliphatic substituents contains from about 8 to 18 carbon atoms and one contains an anionic water solubilizing group, e.g., sulfate or sulfonate. Specific suitable ampholytic surfactants are sodium-3-dodecylaminopropionate and sodium-3-dodecylaminopropane sulfonate.

Examples of suitable zwitterionic surfactants are derivatives of aliphatic quaternary ammonium compounds in which one of the aliphatic constituents contains from about 8 to 18 carbon atoms and one contains an anionic water solubilizing group. Specific examples of zwitterionic surfactants are 3-(N,N-dimethyl-N-hexadecylammonio)propane-1-sulfonate and 3-(N,N-dimethyl-N-hexadecylammonio)-2-hydroxypropane-1-sulfonate.

Suitable surfactants besides those specifically described above are described in "Detergents and Emulsifiers - 1975 Annular," John W. McCutcheon, Inc.

Compositions for use within the scope of the present invention in liquid form (for example, for spraying on fruit bearing plants under superatmospheric pressure as aerosols or mists) are readily prepared for application by admixing abscission agent, surfactant (if used) and liquid carrier (water or other polar liquid) to form a stable emulsion or suspension with the concentration of abscission agent within the range as specified above and the weight ratio of abscission agent to surfactant within the range as specified above.

Compositions for admixture with water just prior to application are very desirable as these compositions are more economically packaged and shipped. Such compositions can be in the form of a solid (a wettable powder) or in the form of a liquid (suspension or emulsion) wherein the carrier is a minor proportion. These compositions preferably comprise (*a*) agent having the structural formula

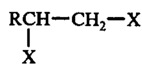

wherein R is an alkyl group having 8–10 carbon atoms and both X's are the same and are selected from the group consisting of thiomethyl (i.e.,—$SCH_3$), thioethyl (i.e.,—$SC_2H_5$), sulfinylmethyl (i.e., $$-\overset{O}{\overset{\uparrow}{S}}CH_3),$$

sulfinylethyl (i.e., $$-\overset{O}{\overset{\uparrow}{S}}C_2H_5),$$

sulfonylmethyl (i.e.,

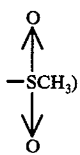

and sulfonylethyl (i.e.,

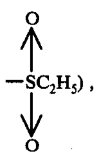

(*b*)non-phytoxic surfactant different from said agent (said surfactants being described in more detail above), the weight ratio of (*a*) to (*b*) ranging from about 1:400 to about 10:1, and (*c*) from 9% to about 20% by weight liquid carrier, preferably water.

Compositions for use in the form of dusts can be prepared by grinding or blending the solid abscission agents herein with a solid carrier such as talc, clay, silica, pyrophyllite or solid fertilizers. Granular compositions can be prepared by impregnating the abscission agents (dispersed or dissolved if normally solid) onto or into granulated carriers such as attapulgites or vermiculites, or granulated solid fertilizers.

The abscission agents herein are also advantageously used in plant-substantive formulations. The term "plant-substantive" is used herein to encompass formulations which mechanically or chemically adhere to the plant thereby resisting removal. Preferred materials suggested as plantsubstantive agents include various waxes and paraffins, polymers, and sulfur. Wax coated active can be prepared by dispersing the active ingredients in molten wax, forming the dispersion into small particles, and cooling the composition below the melting point of the wax. The water resistance of the particles can be controlled by increasing or decreasing the amount of wax employed so as to provide proper release for climatic conditions encountered. In areas of relatively heavy rainfall, the water resistance should normally be high and the amount of wax in the dispersion should be relatively high also. Conversely, in relatively dry areas the amount of wax should be relatively low. In addition, various additives can be dissolved in the wax phase in order to improve the water resistance of the composition or effect other benefits. U.S. Pat. No. 3,252,786, incorporated herein by reference, discloses the use of rosins or asphalts as effective slow-release additives. Other additives can be used, for example, to provide anticaking properties. Elemental sulfur is an essential plant nutrient in many areas. Thus, its use as a coating agent provides additional nutritive benefits. Sulfur coatings, however, tend to be very porous and present serious leaching problems. Therefore, sulfur-coated compositions usually contain a sealant material, for example petrolatum or waxes.

The compositions for use herein advantageously additionally include a safe and effective amount of other biologically active adjuvants. As used herein the term "biologically active adjuvant" includes insecticides, fungicides, herbicides, fertilizers, antimicrobial agents, and the like. The selection of adjuvants depends primarily upon the needs of the individual user. The preferred adjuvants for use herein are herbicides, insecticides, antimicrobial agents and fertilizers.

The above described invention is illustrated in the following two specific examples. In each of the following examples I and II, the procedure was as follows: Abscission agent and surfactant were admixed with water to provide an aqueous formulation of 500 milliliters. This 500 milliliters of formulation was sprayed over an orange tree branch containing about 20 fruit. A week later, 10 fruit were removed from the treated branch with the stems still attached, and the force required to separate each of the fruit from the attached stem was measured utilizing a pull tester. An average force was calculated by adding up the forces of each of the 10 pulls and dividing by 10. A control test was also carried out where no abscission agent was applied. In the control test (which was carried out in respect to Valencia oranges), the average force required to pull each orange was about 20 pounds, and in the case of 30% of the oranges, rind was torn off as a result of the pull. The results in the examples below are compared to these control results to determine the magnitude of the effect of the abscission agent. A test result of the fruit being too loose to pull (that is, the force required to remove the fruit was too small to measure), demonstrates the maximum improvement within the framework of the test.

The following examples are illustrative of the scope of the invention and are not to be construed in any way as limiting the scope of the invention.

EXAMPLE I

A 500 milliliter aqueous formulation was made up utilizing 2 grams of 1,2-bis(sulfinylmethyl)dodecane (the above structural formula where R is an alkyl group having 10 carbon atoms and X is sulfinylmethyl) and 5 grams of Surfactant X-77 (a mixture comprising alkylaryl polyoxyethylene glycols, free fatty acids and isopropanol - available from Colloidal Products Corporation). It was applied to Valencia oranges. The composition applied contained 4000 parts per million of abscission agent. The application of the 500 milliliters to one branch was equivalent to applying 16-32 pounds of abscission agent per acre. The average pull force determined was 2.8 pounds. In no case was the rind torn.

The above test was repeated. The fruit were too loose to pull.

Similar results are obtained when 1,2-bis(sulfinylethyl)dodecane is substituted for 1,2-bis(sulfinylmethyl)dodecane.

EXAMPLE II

A 500 milliliter aqueous formulation was made up utilizing 2 grams of 1,2-bis(thiomethyl)dodecane (the above structural formula where R is an alkyl group having 10 carbon atoms and X is thiomethyl) and 5 grams of Surfactant X-77. It was applied to Valencia oranges. The composition applied contained 4000 parts per million of abscission agent. The application of the 500 milliliters to one branch was equivalent to applying 16–32 pounds of abscission agent per acre. The average pull force determined was 7.2 pounds. In no case was the rind torn.

The above test was repeated. The average pull force determined was 9.5 pounds. In no case was the rind torn.

When in the above example, 2 grams of 1,2-bis(thioethyl)dodecane, 1,2-bis(thiomethyl)decane, 1,2-bis(thioethyl)decane, 1,2-bis(thiomethyl)undecane, 1,2-bis(thioethyl)undecane, 1,2-bis(sulfinylmethyl)decane, 1,2-bis(-sulfinylethyl)decane, 1,2-bis(sulfinylmethyl)undecane, 1,2-bis(sulfinylethyl)undecane, 1,2-bis(sulfonylmethyl)-decane, 1,2-bis(sulfonylethyl)decane, 1,2-bis(sulfonylmethyl)undecane, 1,2-bis(sulfonylethyl)undecane, 1,2-bis(sulfonylmethyl)dodecane, 1,2-bis(sulfonylethyl)dodecane is substituted for the 2 grams of 1,2-bis(thiomethyl)dodecane, abscission activity is obtained.

When in the above examples, the surfactant (Surfactant X-77) is omitted, abscission activity is still present.

When in the above examples, other surfactants are utilized instead of Surfactant X-77, such as sodium dodecylbenzene sulfonate, dimethyldidodecylammonium chloride, sodium-3-dodecylaminopropionate or 3-(N,N-dimethyl-N-hexadecylammonio)propane-1-sulfonate, equally good abscission results are obtained.

When in the above examples, the formulations are applied to other types of oranges (e.g., Hamlin oranges) or to other fruit bearing plants (for example to plants bearing citrus fruits such as lemons or grapefruit), abscission activity is realized.

The following examples illustrate compositions for admixture with water or other polar liquid just prior to use:

EXAMPLE III

| | parts by weight |
|---|---|
| 1,2-bis(sulfinylmethyl)dodecane | 1 |
| Surfactant X-77 | 10 |

EXAMPLE IV

| | parts by weight |
|---|---|
| 1,2-bis(sulfinylethyl)dodecane | 1 |
| Surfactant X-77 | 13.7 |
| Water | 10 |

EXAMPLE V

| | parts by weight |
|---|---|
| 1,2-bis(thiomethyl)dodecane | 1 |
| Polyoxyethylene condensate of nonylphenol wherein the amount of ethylene oxide condensed onto each mole of nonylphenol is 10 moles | 10 |
| Water | 2 |

EXAMPLE VI

| | parts by weight |
|---|---|
| 1,2-bis(thioethyl)dodecane | 1 |
| Sodium dodecylbenzene sulfonate | 2½ |
| Water | 0.5 |

The following examples illustrate the preparation of abscission agents within the scope of the invention:

EXAMPLE VII 1-dodecyne (1 mole) and methyl mercaptan (2.1 moles) are placed in an autoclave along with 2 grams of 2,2′-azobis(2-methylpropionitrile) catalyst. The system is pressurized to approximately 1000 psig and heated to 100° C and maintained at 100° C for 4 hours. The resulting crude product is distilled (at 0.02 mm Hg.) to recover substantially pure 1,2-bis(thiomethyl)dodecane (B.P. of 123°–125° C). The same procedure can be used to prepare 1,2-bis(thioethyl)dodecane by substituting ethyl mercaptan for methyl mercaptan in the foregoing procedure.

EXAMPLE VIII 1,2-bis(thiomethyl)dodecane prepared as in Example VII (1.0 mole) is vigorously agitated in an ethanol solution at room temperature. 30% hydrogen peroxide (2.5 moles) is slowly added, and the reaction is stirred overnight. Excess peroxide is then decomposed with platinum on carbon and the alcohol is removed to yield 1,2-bis(sulfinylmethyl)dodecane (a while solid).

EXAMPLE IX 1,2-bis(thiomethyl)dodecane prepared as in Example VII (1.0 mole) is vigorously agitated in an ethanol solution at room temperature. Sodium hypochlorite (5.25% solution) (3.0 moles) is slowly added and the reaction is stirred overnight. The solid 1,2-bis(sulfonylmethyl)dodecane is filtered off and washed with ice water to remove excess sodium hypochlorite.

The term "fruit bearing plant" is used herein to include the major types of fruit, for example, berries such as grapes, tomatoes, blueberries, and oranges; drupes such as peaches, cherries, olives, plums and walnuts; aggregate fruits such as blackberries and raspberries; and multiple fruits such as pineapples, figs and mulberries; and accessory fruits such as apples, pears and strawberries. A thorough description of various other fruit bearing plants which may be treated in accordance with the present invention can be found in General Botany, Fuller and Richie, Barnes and Noble Inc. 1969, incorporated herein by reference.

The invention may be embodied in other specific forms without departing from the spirit or essential characteristics thereof. In view of the variations that are readily understood to come within the limits of the invention, such limits are defined by the scope of the claims.

What is claimed is:

1. A method of inducing fruit abscission comprising applying to fruit bearing plants an effective amount of agent having the structural formula

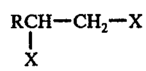

wherein R is an alkyl group having 8–10 carbon atoms and both X's are the same and are selected from the group consisting of thiomethyl, thioethyl, sulfinylmethyl, sulfinylethyl, sulfonylmethyl and sulfonylethyl.

2. The method of claim 1 wherein the agent applied has the structural formula

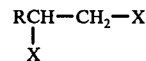

wherein R is an alkyl group containing 10 carbon atoms and X is selected from the group consisting of thiomethyl, sulfinylmethyl and sulfonylmethyl.

3. The method of claim 2 wherein the agent applied is 1,2-bis(sulfinylmethyl)dodecane.

4. The method of claim 2 wherein the agent applied is 1,2-bis(thiomethyl)dodecane.

5. The method of claim 1 wherein said agent is applied in an amount in the range of about 0.1 to 50 lbs./acre.

6. The method of claim 1 comprising also applying to the fruit bearing plants non-phytotoxic surfactant different from said agent.

7. The method of claim 6 wherein the weight ratio of said agent to said surfactant ranges from about 1:400 to about 10:1.

8. The method of claim 1 wherein the fruit is a citrus fruit.

9. The method of claim 8 wherein the plants are orange trees.

* * * * *